United States Patent

Mecikalski

Patent Number: 5,318,016
Date of Patent: Jun. 7, 1994

[54] INHALATION DEVICE

[75] Inventor: Mark B. Mecikalski, Tucson, Ariz.

[73] Assignee: WE Pharmaceuticals, Inc., Ramona, Calif.

[21] Appl. No.: 39,920

[22] Filed: Mar. 30, 1993

[51] Int. Cl.$^5$ .............................. A61M 11/00
[52] U.S. Cl. .................. 128/200.23; 128/200.14; 128/203.28; 128/203.12; 222/162
[58] Field of Search ............ 128/200.14, 200.23, 128/205.13, 203.12, 203.28, 200.22, 200.24, 203.13, 203.14, 203.15, 203.23; 604/319; 222/162

[56] References Cited

U.S. PATENT DOCUMENTS

| | | | |
|---|---|---|---|
| 3,530,857 | 9/1970 | Miczka | 128/205.13 |
| 4,484,577 | 11/1984 | Sackner et al. | 128/203.28 |
| 4,796,614 | 1/1989 | Nowacki et al. | 128/200.14 |
| 4,846,168 | 7/1989 | Abiko et al. | 128/203.15 |
| 4,865,027 | 9/1989 | Laanen et al. | 128/200.21 |
| 4,926,852 | 5/1990 | Zoltan et al. | 128/200.23 |
| 4,938,210 | 7/1990 | Shene | 128/203.12 |
| 4,940,051 | 7/1990 | Lankinen | 128/200.18 |
| 4,953,545 | 9/1990 | McCarty | 128/200.23 |
| 5,020,530 | 6/1991 | Miller | 128/203.28 |
| 5,027,806 | 7/1991 | Zoltan et al. | 128/200.23 |
| 5,040,527 | 8/1991 | Larson et al. | 128/200.23 |
| 5,203,323 | 4/1993 | Tritle | 128/200.23 |

*Primary Examiner*—Edgar S. Burr
*Assistant Examiner*—Eric P. Raciti
*Attorney, Agent, or Firm*—Juettner Pyle & Lloyd

[57] ABSTRACT

A therapeutic inhalation device for receiving a dose of oronasal medication from a pressurized aerosol source and for delivering the same in dispersed and nonpressurized form to a breathing passage of a patient is comprised of top and bottom members and a collapsible sleeve attached at its opposite ends to the top and bottom members and defining therewith a spacer or breathing chamber that is extendable and contractible. The bottom member is cup-shaped and of a size to receive the sleeve and top member when the sleeve is collapsed and the top member is inserted into the bottom member, thereby to provide a device which, when not in use, is small and compact and conveniently stored and transported. The top member is provided with a guide member for positioning a medication containing aerosol canister for dispensing of its contents into the spacer chamber and an inhalation member communicating with the chamber for delivery of the medication to the patient in the form of a non-pressurized dilute dispersion. The guide and inhalation members are movable to retracted storage positions within the top member for convenience of storage and transportation.

15 Claims, 4 Drawing Sheets

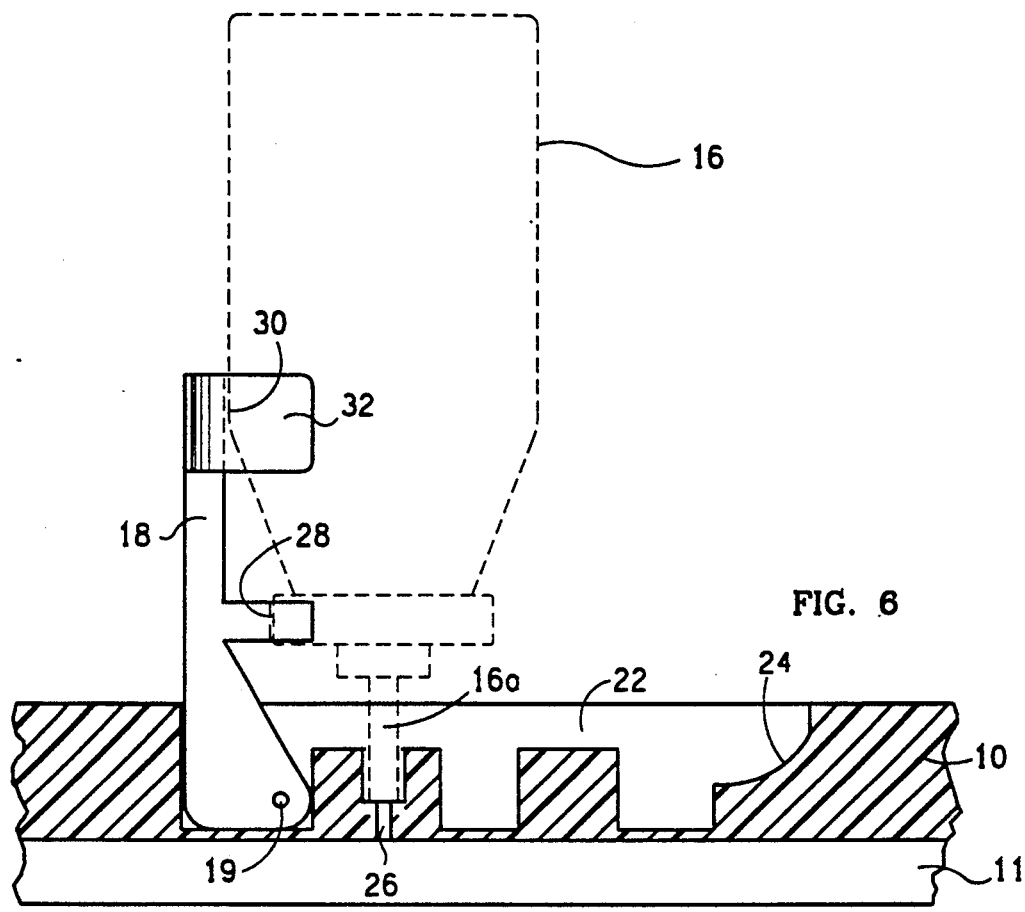
FIG. 6
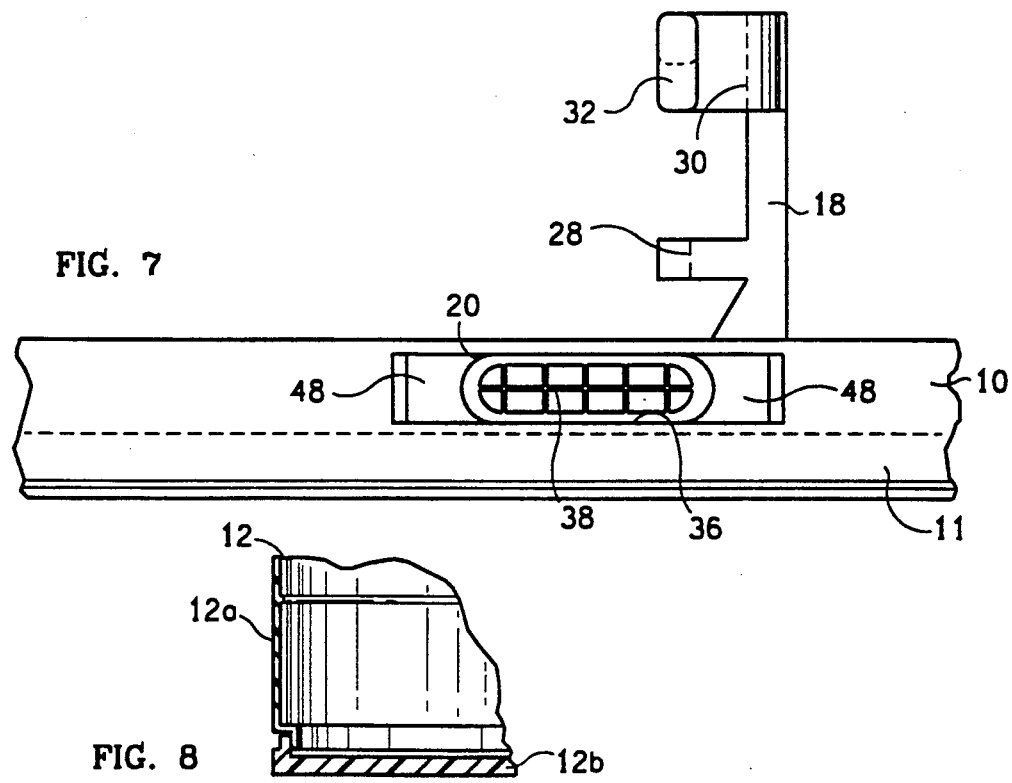
FIG. 7
FIG. 8

INHALATION DEVICE

FIELD OF THE INVENTION

The present invention relates to inhalation devices or so-called spacers for administering oral nasal medications, and more particularly to devices for converting medications for treatment of tracheal, bronchial, nasal and pulmonary conditions from a concentrated pressurized aerosol form into a nonpressurized, air diluted form for ease and greater efficacy of inhalation by a patient suffering from such a condition.

BACKGROUND

Oronasal delivery of drugs has long been known and has gained wide acceptance. Pharmaceuticals for the treatment of tracheal, bronchial, nasal and pulmonary conditions are widely available in prescribed or metered doses in small pressurized aerosol canisters. While medications can be dispensed directly from such canisters into the oronasal passages of patients, experience has proven that patients generally have not made optimum use of and/or have not obtained optimum benefits from medications delivered directly from the aerosol canisters. In this regard, reference may be had to the introductory or background portion of U.S. Pat. No. 4,484,577.

Because direct use of the aerosol canisters has not proven effective or efficient for a large proportion of patients, many devices have been proposed for converting the medications from the concentrated pressurized form in which they are discharged from aerosol canisters into a nonpressurized and less concentrated form in order to be more readily and efficaciously inhaled by the patient. Further, it has been found that a long and slow inspiration of the mediation promotes a highly efficient distribution of medication to partially occluded airways. Thus, it is desirable in such devices to inhibit rapid inhalation and to encourage a long and slow inspiration period; reference in this regard again being had to U.S. Pat. No. 4,484,577.

In order to promote a long and slow inspiration period, it is desirable to provide an expandable and contractible breathing bag or spacer, so that the patient is required during respiratory maneuvers to utilize a negative thoracic pressure upon inhalation, thereby to inhibit rapid inhalation and encourage long and slow inhalation. Representative prior art devices having expandable and contractible breathing bags or spacer chambers may be found by way of example, in U.S. Pat. Nos. 4,938,210, 4,940,051 and 5,040,527, as well as U.S. Pat. No. 4,484,577.

While some of these devices have enjoyed fairly widespread acceptance and use, a major problem with the same resides in the fact that they are quite bulky and cannot conveniently be carried about or transported by a patient when leaving home or going on a trip.

SUMMARY OF THE INVENTION

A primary object of the present invention is to provide a therapeutic inhalation device that includes an expandable and contractable medication receiving beathing bag or spacer chamber for encouraging long and slow inhalation of the medication by the patient and that nevertheless is small, compact and lightweight, and may conveniently be carried about, stored and transported when not in use.

Another object of the invention is to provide a therapeutic inhalation device which includes a housing member within which the spacer chamber means and all other of the components of the device may be compactly stored so that the device may conveniently and safely be carried about in a pocket or a purse.

A further object of the invention is to provide a therapeutic inhalation device as above described wherein the means for injecting the medication into the spacer or breathing chamber and for dispensing the medication to the patient are movably mounted on the spacer or breathing chamber means for movement between extended operative positions and retracted stored positions, thereby further to contribute to the compactness of the device so that the device may conveniently and safely be carried about, stored and transported.

A still further object of the invention is to provide a therapeutic inhalation device that is of economical and practical construction.

It is in particular an object of the invention to provide a new and improved therapeutic inhalation device including a top member forming one wall of a spacer or breathing chamber and including extendable and retractable means for receiving a measured dose of medication from an aerosol canister and for administering the medication to a patient, a bottom member forming another wall of the spacer chamber, and an expandable and contractible flexible sleeve attached at its opposite ends to said top and bottom members for completing the spacer or breathing chamber; said top member having recesses therein for storage of said receiving and dispensing means in retracted positions, and said bottom member comprising a housing for compact reception and storage of said sleeve and said top member, thereby to provide a device of optimum therapeutic efficacy which, when not in use, is very small and compact.

These and other objects and advantages of the invention will become apparent from the following detailed description, as considered in conjunction with the accompanying drawings.

BRIEF DESCRIPTION OF THE DRAWINGS

FIG. 6 is a cross sectional view of the top member of the device as taken on line 6—6 of FIG. 4;

FIG. 7 is a fragmentary side view of the top member of the device;

FIG. 8 is a fragmentary cross sectional view of the bottom member of the device.

DETAILED DESCRIPTION

Figure 1:
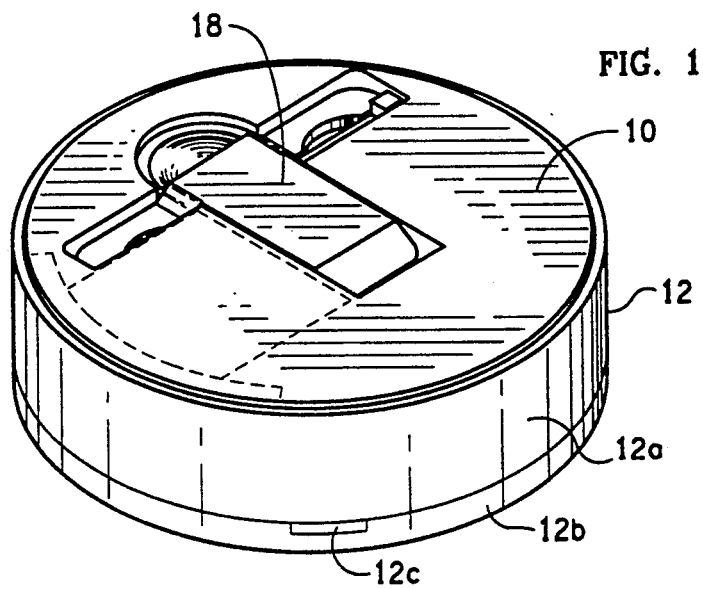
FIG. 1 is a perspective view of a preferred embodiment of the inhalation device of the invention in its compact, closed position for convenience of storage and transportation.

The following is a detailed description of a preferred embodiment of the inhalation device of the invention that is presently contemplated by the inventor as being the best mode of carrying out his invention.

Referring to the drawings, the inhalation device of the invention includes a top mounting member 10, a bottom member 12 and a flexible sleeve 14 which is attached at its opposite ends to said top and bottom members, respectively. The sleeve is collapsible and extendable and with the top and bottom members defines an expandable and retractable air bag or spacer chamber for receiving a dose of medication (usually a fine powder) in pressurized form from an aerosol canister, such as the canister 16 illustrated in dotted lines in FIG. 3, and for delivering the medication in an air diluted and nonpressurized form to the oronasal breathing passages of a human patient.

Figure 2:
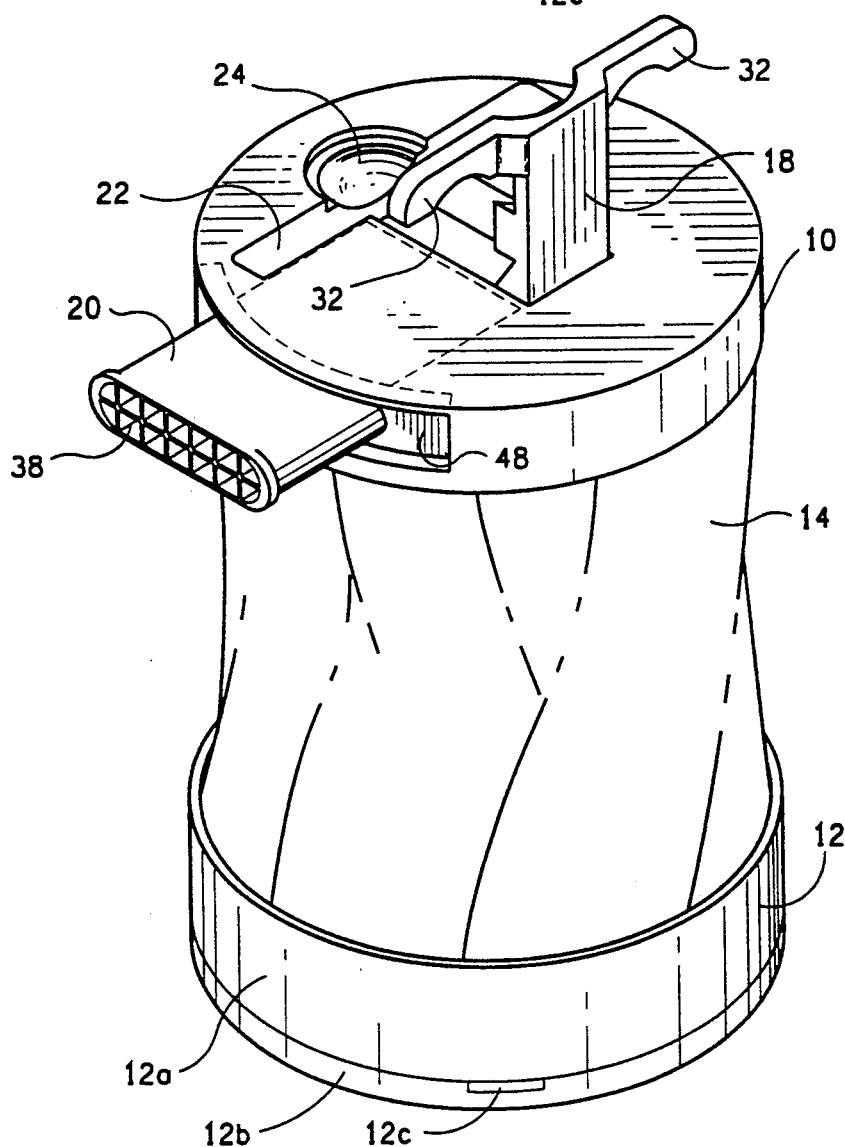
FIG. 2 is a perspective view of the device illustrated in FIG. 1 in its extended or expanded position ready for use.
Figure 3:
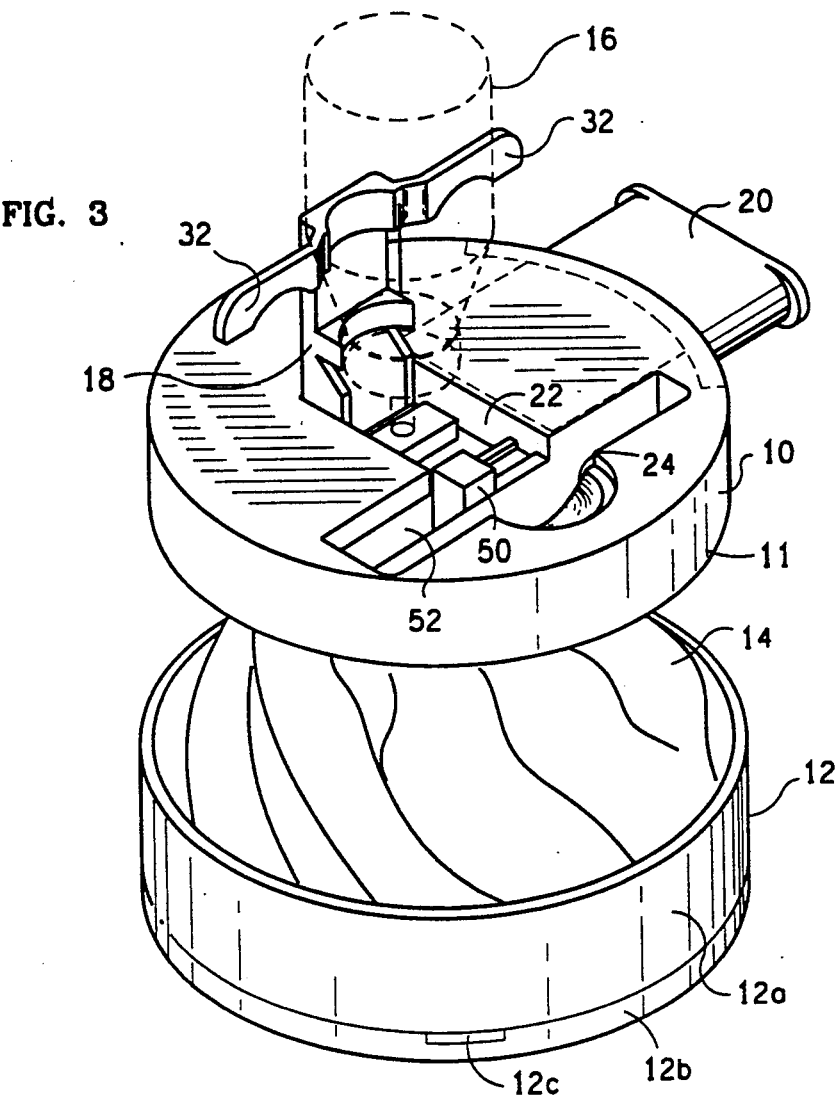
FIG. 3 is a perspective view from a different angle, of the device illustrated in FIG. 2 showing the same with the air bag or spacer chamber partially collapsed, and illustrating in dotted lines the manner in which a medication containing aerosol canister may be associated with the device.

As illustrated in FIG. 1, the bottom member 12 is of cup shape and of a size to receive therein the top member 10 and the sleeve 14 when the sleeve is collapsed upon itself. To facilitate compact collapse and storage thereof, the sleeve 14 preferably has a spiral bias imparted to it, by twisting the same as indicated in FIGS. 2 and 3, so that the same will fold up very neatly when the members 10 and 12 are moved toward and rotated slightly relative to one another. The rotational aspect of relative movement between the top and bottom members renders a cylindrical shape for the two members preferable, though not essential. Also, a cylindrical shape is particularly convenient when the device is to be carried about or transported in a person's pocket or purse.

To prevent inadvertent separation of the members 10 and 12 during transport, the same are preferably provided on their mating cylindrical surfaces with cooperating annular beads or detents (see FIGS. 5 and 8) which releasably secure the top member within the bottom member.

The sleeve 14 is preferably comprised of an air impervious, durable, flexible plastic tube or sheet material that is readily cleansed and sterilized. The top and bottom members are likewise preferably molded or otherwise formed from plastic materials that are durable and readily cleansed and sterilized. The sleeve 14 may be attached to the top and bottom members in any known manner. However, it is preferable to affix the top of the sleeve to the interior surface of the peripheral skirt 11 of the top member 10, suitably by an adhesive, so as to form an air tight seal between the same. Similarly, the bottom of the sleeve is preferably adhesively sealed and secured to the interior of the cylindrical side wall of the cup shaped bottom member 12.

To accommodate convenient cleansing of the air bag or spacer chamber, the bottom member 12 is preferably made of two piece construction. Specifically, as shown in FIG. 8, the bottom member 12 is preferably comprised of a cylindrical side wall member 12a and a removable bottom closure 12b that has a very snug press fit onto the bottom of the side wall member 12a. These two parts are preferably formed of molded plastic which has a modest degree of yield or flexibility so that the parts may include cooperating beads or detent means permitting the two members to be snapped together in a releasably locked condition. To facilitate separation of the two parts or components, in order to gain access to the spacer chamber for cleansing the same, the bottom closure 12b is provided with one or more coin slots 12c in its upper edge so that a coin can be inserted between the two parts and twisted to effect separation of the bottom closure. After cleansing of the chamber, the closure 12b can be pressed back onto the base of the side wall member 12a to restore the device to operative condition.

The top member 10 is relatively thick and may be molded or machined from a durable substantially rigid plastic material. The member 10 has recesses therein and comprises a mounting member for the reception of retractable and extendable medication receiving and delivering members; specifically an aerosol canister guide 18 and an inhalation member 20.

The aerosol canister guide 18 is pivotally mounted by a pivot pin 19 on the top wall of the member 10 for movement between a retracted position shown in FIG. 1, wherein the guide is generally parallel with the top wall of the member 10, and an extended or upright position shown in the remainder of the FIGURES, wherein the guide extends generally normal or perpendicular to the top wall of the member 10. A recess 22 is provided in the top wall of the member 10 for conformable reception therein of the guide 18 so that the guide is wholly housed within the confines of the member 10 when the guide is in its retracted position, as illustrated in FIG. 1. To accommodate access to the guide for movement from its retracted position to its extended position, the recess 22 also includes an upwardly open finger depression 24 so that a user may engage the outer edge of the guide 18 with a finger to effect movement of the same to its upright position. The recess 22 is so configured relative to the guide that interference fits or detent means are defined between the same so as to releasably retain the guide in both its retracted position and its extended position.

An aerosol injection port or aperture 26 extends vertically through the top mounting member 10 and into the spacer chamber from a position within the recess 22. The port or aperture has an upper end portion of a size to receive the dispensing nozzle 16a of an aerosol canister 16, a lower end portion of a size smaller than the nozzle, and an intervening shoulder on which such nozzle is adapted to rest, all as is illustrated in FIG. 6. Thus, as is known in the art, upon exertion of force vertically downwardly on the body of the canister 16, the nozzle will open and the contents of the canister will be discharged through the port or aperture 26 into the interior of the spacer chamber or air bag defined by the members 10 and 12 and the sleeve 14.

To facilitate discharge of the contents of the canister as above described, the guide 18 includes at least one and preferably two arcuate surfaces for positioning and guiding the canister. With the guide in its extended upright position, as illustrated in FIGS. 3-6, each arcuate surface comprises an arc of a circle concentric with the axis of the injection port or aperture 26 and of a diameter substantially equal to the diameter of a respective surface on the canister. As shown in FIG. 6, the guide 18 is preferably provided with a first or lower arcuate guiding surface 28 conforming to and receiving the neck of the canister and a second or upper arcuate guiding surface 30 conforming to and receiving the body of the canister.

For purposes of supporting or holding the device in its expanded and operative position, the guide 18 is provided with a pair of finger grips 32 extending outwardly in opposite directions from the upper or outer end of the guide, i.e., at opposite sides of the upper guiding surface 30. With the guide member 18 in its extended or upright position, the user-patient may insert two fingers under the grips 32 and use the same to extract or remove the top member and the sleeve from their stored positions within the bottom member 12 (FIG. 1) and to support the inhalation device in its extended or expanded condition (FIG. 2). With the inhalation device thus supported by two fingers of one of the patient's hands, the patient may use the other hand to insert an aerosol canister into dispensing position on the top member 10, as is illustrated in FIGS. 3 and 6. The user-patient may then utilize such other hand or the thumb or another finger on the hand that is supporting the device by the grips 32 to engage the base of the canister and press the body of the canister downward to open the nozzle and cause the contents of the canister to be discharged into the extended or expanded spacer chamber or breathing bag.

Upon discharge of the contents of the aerosol canister into the breathing chamber or bag, which has a volumetric capacity far greater than that of the canister, the contents are dispersed throughout the chamber into a nonconcentrated or dilute dispersion suspended in the air in the chamber. Also, the gaseous pressure under which the medication was stored in the canister is dissipated in the chamber and the medication is dispersed in non pressurized form, i.e., at ambient pressure.

Figure 4:
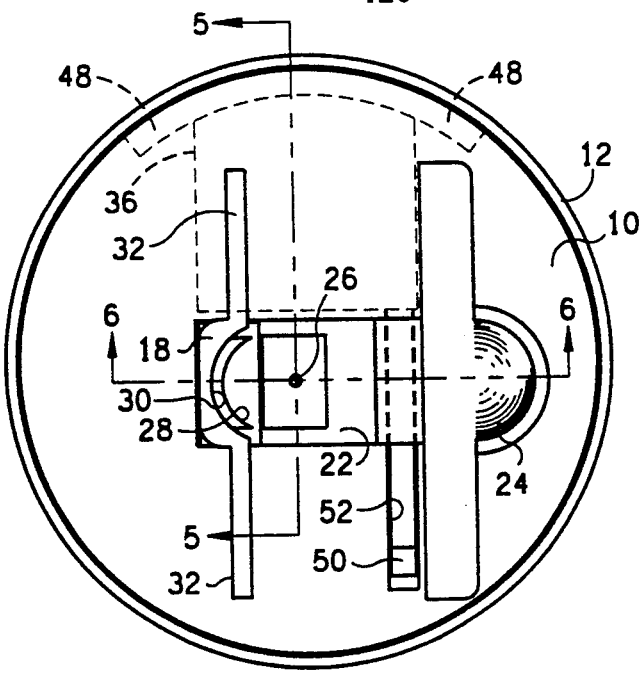
FIG. 4 is a top plan view of the device as viewed from the top of FIG. 3.
Figure 5:
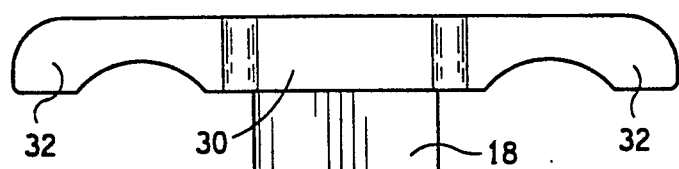
FIG. 5 is a cross sectional view of the top member of the device as taken on line 5—5 of FIG. 4.
Figure 9:
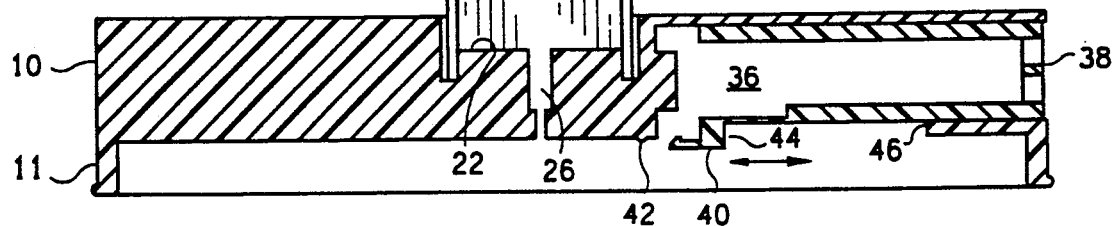
FIG. 9 is a perspective view similar to FIG. 3 showing the manner in which an oronasal inhalation face mask may be associated with the device.

To facilitate inhalation of the dispersion of medication in the spacer or breathing chamber, the top member 10 is provided with inhalation member 20 which may be used directly for oral inhalation or in combination with a face mask for oronasal or nasal inhalation. As shown in FIG. 5, the top member 10 is provided with a horizontally extending cavity 36 which opens horizontally through the side wall of the member 10, preferably at a location spaced 90 degrees from the location of the canister guide so as not to interfere with or intersect the guide receiving recesses 22 in the top member 10. The inhalation member 20, which is preferably in the form of a rectangular tube, is slidably and conformably received within the cavity 36 for movement between a stored position wherein it is wholly housed within the top member, as illustrated in FIGS. 4 and 5, and an extended position of use wherein it extends laterally outward from the side of the top member, as illustrated in FIGS. 2, 3 and 9. A rectangular tube with rounded edges is preferred, as such shape most closely conforms to the shape of a patient's mouth and facilitates dispersion of the medication throughout the breathing passages. The member 20 is provided within its interior with a grid work 38 for preventing ingress of foreign objects when the device is carried in a pocket or purse, and for preventing inhalation of any such foreign object by the patient.

As is shown in FIG. 5, the cavity 36 is downwardly open interiorly of the side wall portion of the top member 10 so as to establish communication between the interior of the inhalation member and the interior of the breathing bag or spacer chamber.

Also as is shown in FIG. 5, the inhalation member 20 is provided at its inner end with a depending detent member 40 including a latch which is adapted to engage with a bead 42 on the lower surface of the top member to releasably lock the inhalation member in its stored position within the cavity 36. The detent member 40 also forms a shoulder 44 which is adapted to abut against a lip 46 on the top member at the outer edge of the downwardly open portion of the cavity 36, thereby to position the inhalation member in its extended position of use and to prevent inadvertent removal of the inhalation member 20 from the top member 10. However, when the bottom closure 12b is removed, the detent member 40 can be pressed upwardly to cause the shoulder 44 to clear the lip 46 and thereby permit removal of the member 20 for purposes of hygienic cleansing.

To accommodate access to the inhalation member 20 for movement from its stored position within the top member 10 to its outwardly extended position of use, finger indentations 48 are provided in the side wall of the top member at opposite sides of the cavity 36 to accommodate grasping of the member 20 to extract the same from its stored position. In addition, or in the alternative, if it is desired to avoid touching the inhalation member, an actuator slide 50 is provided for moving the inhalation member between its stored and extended positions. The actuator comprises an abutment member slidably mounted in an upwardly open slot 52 in the upper surface of the mounting member 10 and a wand extended from the abutment to the inhalation member and detachably secured at its opposite ends, as by a press fit, to the abutment and the inhalation member so that manipulation of the abutment will cause the inhalation member to be moved between its stored and extended positions. Due to the detachable engagement of the actuator therewith, the inhalation member may still be removed from the top member for purposes of cleansing.

As noted in the foregoing, the inhalation member 20 may be inserted in the patient's mouth and utilized directly for purposes of oral inhalation of the nonpressurized dispersion of medication in the breathing chamber. If oronasal or nasal inhalation is prescribed, a face mask 60 of conventional form may be detachably secured to the member 20, as illustrated in FIG. 9. For the purpose, the mask is equipped at its inlet with a flexible sealing member 62 having a slot 64 therein of a size and shape for conformable reception and sealed engagement with the outer end portion of the inhalation member 20.

In use, the device of the invention provides an expansible and contractible breathing chamber of relatively large volume for reception of a medication from an aerosol canister and for uniform dispersion of the medication in relatively dilute and nonpressurized form within the chamber. In order to inhale the dispersed medication from the chamber, the patient must exert a negative thoracic pressure at the inhalation member in order to collapse the breathing chamber and induce the flow of medication from the chamber into the patient's breathing passages. This in turn encourages and promotes a long and slow inspiration period in order to obtain maximum utilization of the medication and maximum efficacy from the therapeutic exercise.

In order to collapse the breathing chamber, the patient must exert sufficient negative pressure within the chamber to move the bottom member 12 up to the top member 10 solely by negative thoracic pressure without mechanical or manual assistance. This in turn suggests that in order to induce a patient to develop and exert a desired level of negative thoracic pressure, and to employ a long and slow period for inspiration of the medication, it may prove feasible to vary and adjust the weight of the bottom member, e.g., the bottom closure 12b, to meet the particular needs of a given patient.

The size and volumetric capacity of the breathing chamber may also be adjusted to meet the varying needs of various patients by producing the inhalation device of the invention in different diameters and/or with collapsible sleeves 14 of various lengths.

In all cases, however, the device is readily collapsed into a compact and conveniently transported package so that the same may be carried about by the patient for use whenever the occasion or circumstances demand. Specifically, the inhalation member 20 is slidably movable into a wholly retracted and stored position within the cavity 36 in the top member 10, the guide 18 is pivotally movable into a wholly retracted and stored position within the recess 22 in the top surface of the member 10, the sleeve 14 is collapsible into the bottom member 12, and the top member 10 is movable into and wholly stored within the bottom member 12, thereby to assume the extremely compact position illustrated in FIG. 1.

The objects and advantages of the invention have thus been shown to be attained in a convenient, economical, practical and facile manner.

While a preferred embodiment of the invention has been herein illustrated and described, it is to be appreciated that various changes, rearrangements and modifications may be made therein without departing from the scope of the invention as defined by the appended claims.

What is claimed is:

1. In an inhalation device having an expandable and contractible breathing chamber for receiving a dose of medication from a dispensing nozzle of an aerosol canister and for delivering medication in dispersed and non-pressurized form to a breathing passage of a patient, improved means for reception of the canister and discharge of its contents into the breathing chamber comprising a mounting member forming a wall portion of the breathing chamber and having an interior surface and an exterior surface, an aperture through said member leading from said exterior surface to said interior surface and communicating with the breathing chamber, said aperture accommodating reception therein of the dispensing nozzle of the canister, a guide member pivotally mounted on the exterior surface of said mounting member for movement between a retracted storage position generally parallel with said mounting member and an extended position generally normal to said mounting member, said guide member having thereon at least one guiding surface which in the extended position of said guide member forms an arc of a circle concentric with the axis of said aperture and of a diameter corresponding to the diameter of a surface portion of the canister, said guide member including finger grip portions extending outwardly in opposite directions from said guiding surface for receiving two fingers of a user and for accommodating the exertion of pressure by the user onto a canister having its dispensing nozzle inserted in said aperture and a surface portion thereof engaged with said guiding surface, thereby to cause the contents of the canister to be dispensed into said breathing chamber, said guide member when not in its extended position being pivotally movable to its retracted storage position generally parallel to said mounting member.

2. In a device as set forth in claim 1, the canister having a body and a neck of smaller size than the body, said guide member having at least two guiding surfaces thereon for engagement respectively by the neck and the body of the canister.

3. In a device as set forth in claim 1, said mounting member having recesses in its exterior surface for conformable reception therein of said guide member and said finger grip portions thereof when said guide member is in its retracted storage position.

4. In a device as set forth in claim 1, detent means between said mounting member and said guide member for releasably retaining said guide member in its extended position and for releasably retaining said guide member in its retracted storage position.

5. In a device as set forth in claim 1, said mounting member including a cavity in its interior surface in communication with the breathing chamber and adapted for reception of an inhalation member, and an inhalation member movably mounted in said cavity for movement from a compact retracted storage position within said cavity to an extended position of use protruding from said mounting member.

6. In a device as set forth in claim 5, an actuating member associated with said inhalation member and accessible from the exterior surface of said mounting member for moving said inhalation member between its said retracted position and its said extended position.

7. A device as set forth in claim 5, including a face mask for use in inhalation of the medication, and means on said face mask and said inhalation means for detachably associating said face mask with said inhalation means.

8. An inhalation device for receiving a dose of medication from a dispensing nozzle of an aerosol canister and for delivering the medication in non-pressurized form to a breathing passage of a patient, comprising a top member including an inhalation member, a bottom member, a collapsible sleeve attached at one end to said top member and at its other end to said bottom member, said inhalation member communicating with the interior of said sleeve, said bottom member being of cup shape and of a size to receive said top member and said sleeve when said sleeve is collapsed and said top member is inserted into said cup shaped bottom member, thereby to form a compact device which when not in use is conveniently stored and transported, said top member and said sleeve being removable from said bottom member and said sleeve being extendable to define a breathing chamber for reception of medication from an aerosol canister and for delivery of the medication in nonpressurized form to said inhalation member, and means for dispensing medication from the canister into said breathing chamber comprising an aperture extending through said top member for receiving the dispensing nozzle of the canister and for establishing communication between the nozzle and said breathing chamber, and a guide member pivotally mounted on the upper surface of said top member for movement between a retracted storage position generally parallel to said top member and an extended position generally normal to said top member, said guide member having at least one guiding surface which in the extended position of said guide member forms an arc of a circle concentric with the axis of said aperture and of a diameter corresponding to a surface portion of the canister, said guide member including finger grip portions extending outwardly in opposite directions from said guiding surface for receiving two fingers of a user and for accommodating the exertion of pressure by the user onto a canister having its dispensing nozzle inserted in said aperture and a surface portion thereof engaged with said guiding surface, thereby to cause the contents of the canister to be dispensed into said breathing chamber, said guide member when not in its extended position for dispensing the contents of the canister being pivotally movable to its retracted storage position generally parallel to said mounting member thereby to contribute to the compactness of the device for convenient storage and transportation.

9. A device as set forth in claim 8, one of said top and bottom members having a detachable association with said sleeve and being removable therefrom to accommodate cleaning of the interior of the device.

10. A device as set forth in claim 8, wherein said bottom member is comprised of a sidewall member to which said sleeve is attached and a bottom closure member detachably secured to said sidewall member, said bottom closure member being detachable from said saidewall member to accommodate cleaning of the interior of the device.

11. A device as set forth in claim 8, said top member having recesses in its upper surface for conformable reception therein of said guide member and said finger grip portions thereof when said guide member is moved to its retracted storage position.

12. A device as set forth in claim 8, said inhalation member being movably mounted on said top member for movement between a retracted storage position and an extended position of use.

13. A device as set forth in claim 11, said top member including an internal cavity in communication with said breathing chamber and opening to one side of said top member, said inhalation member being slidably mounted in said cavity for movement between a retracted storage position within said cavity and a laterally extended position of use.

14. A device as set forth in claim 13, including detent means between said top member and said inhalation member for releasably securing said inhalation member in its retracted position within said cavity and for releasably retaining said inhalation member in its extended position of use.

15. A device as set forth in claim 13, including an actuating member associated with said inhalation member and accessible from the exterior of said top member for moving said inhalation member between its said retracted position and its said extended position.

* * * * *